United States Patent [19]

Mori

[11] Patent Number: 4,970,166
[45] Date of Patent: Nov. 13, 1990

[54] BIOREACTOR HAVING A GAS EXHANGER

[76] Inventor: Kei Mori, 3-16-3-501, Kaminoge, Setagaya-ku, Tokyo, Japan

[21] Appl. No.: 54,355

[22] Filed: May 26, 1987

[30] Foreign Application Priority Data

Jul. 3, 1986 [JP] Japan ................ 61-156653

[51] Int. Cl.$^5$ ................................ C12M 1/04
[52] U.S. Cl. ..................... 435/313; 362/32; 435/284
[58] Field of Search ............ 435/284, 286, 289, 291, 435/313, 314, 315, 309; 362/32, 101, 805

[56] References Cited

U.S. PATENT DOCUMENTS

| | | | |
|---|---|---|---|
| 2,815,607 | 12/1957 | Schroeder | 362/32 |
| 3,218,758 | 11/1965 | Konikoff | 435/313 |
| 3,821,087 | 6/1974 | Knazek et al. | 435/313 |
| 4,626,065 | 12/1986 | Mori | 362/32 |
| 4,649,114 | 3/1987 | Miltenburger et al. | 435/284 |
| 4,676,956 | 6/1987 | Mori | 435/315 |

FOREIGN PATENT DOCUMENTS

| | | |
|---|---|---|
| 0052252 | 5/1982 | European Pat. Off. |
| 2093730 | 9/1982 | United Kingdom ............ 435/313 |

Primary Examiner—Noah P. Kamen
Attorney, Agent, or Firm—Jordan and Hamburg

[57] ABSTRACT

A bioreactor comprising a bioreactor tank, a plurality of transparent cylindrical bodies together making up a light radiator and arranged parallel to each other in the bioreactor tank, a plurality of optical conductors inserted into each of the transparent cylindrical bodies, a light source device for guiding into the optical conductors the visible light ray components of solar rays and/or artificial light rays, and a gas-exchanger for supplying carbon dioxide $CO_2$ to a micro-organisms suspension in the space between the transparent cylindrical bodies in the bioreactor. A part of the micro-organisms suspension in the bioreactor is returned to the bioreactor through the gas-exchanger, and carbon dioxide $CO_2$ is supplied to the micro-organisms suspension in the gas-exchanger. The gas-exchanger consists of silicone pipes having microscopic holes through which the returned micro-organisms suspension pass and a hermetically sealed tank into which the silicone pipes are disposed. Carbon dioxide $CO_2$ at a pressure higher than that of the micro-organisms suspension flows into the silicone pipes upon being supplied to the hermetically sealed tank.

5 Claims, 4 Drawing Sheets

BIOREACTOR HAVING A GAS EXHANGER

BACKGROUND OF THE INVENTION

The present invention relates to a bioreactor, in particular, a bioreactor for cultivating chlorella, algae, cellular tissue of plants or animals, and living things (called "micro-organisms" hereinafter).

The present applicant has previously proposed in various ways the cultivation of micro-organisms such as chlorella, algae or the like. However, the cultivation of such chlorella or algae needs light rays and carbon dioxide ($CO_2$) as condition for photo-synthesis to take place. With respect to the light source, the present applicant proposed in various ways methods for supplying light rays consisting of the visible light ray components of solar rays and/or artificial light rays, that is, supplying light rays which do not contain ultraviolet or infrared rays. The present applicant has further proposed a reactor that will not generate phaeophorbite toxin. However, a supply of carbon dioxide $CO_2$ is provided by bubbling it and causing it to blow into the culture fluid. As a result, the cell of micro-organisms is destroyed thereby. In the case of employing a bioreactor in space, such as in a space craft, carbon dioxide $CO_2$ cannot be bubbled in that it would become a mist only. Consequently, it is impossible to dissolve carbon dioxide $CO_2$ in a culture fluid.

SUMMARY OF THE INVENTION

The primary object of the present invention is to provide a bioreactor capable of effectively dissolving carbon dioxide $CO_2$ into a culture fluid.

The above-mentioned features and other advantages of the present invention will be apparent from the following detailed description along with the accompanying drawings.

BRIEF DESCRIPTION OF THE DRAWINGS

FIGS. 5a and 5b are cross-sectional views for explaining the construction of a light radiator installed in the bioreactor, wherein FIG. 5a is a side cross-sectional view of the light radiator and FIG. 5b is a plane view thereof.

DESCRIPTION OF THE PREFERRED EMBODIMENTS

Figure 1:
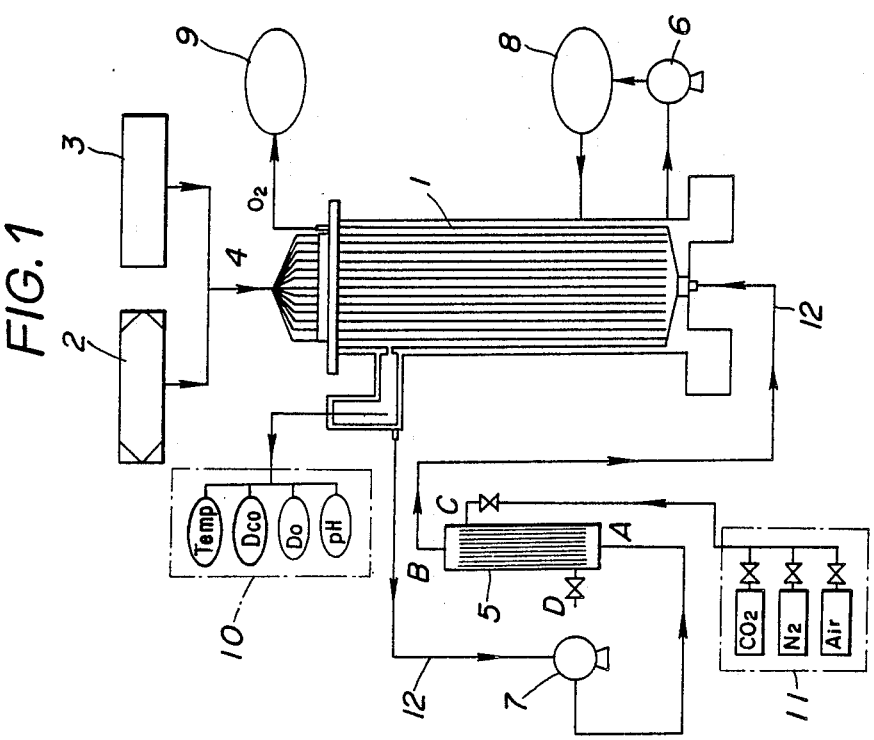
FIG. 1 is an overall construction view for explaining an embodiment of a bioreactor according to the present invention.

FIG. 1 is a construction view for explaining an embodiment of a bioreactor according to the present invention. In FIG. 1, 1 is a bioreactor tank, 2 a solar ray collecting device, 3 an artificial light ray source, 4 an optical conductor such as an optical fiber, etc., 5 a gas-exchanger, 6 and 7 pumps, 8 a density analyzer, 9 an oxygen analyzer and discharger, 10 a culture fluid testing device, and 11 a carbon dioxide supplying device, 12 a feedback flowing passage for a micro-organism suspension or a culture medium.

As is well known, light rays consisting of visible light ray components containing therein neither ultraviolet nor infrared rays are supplied to the bioreactor 1 through the optical conductor 4 from the solar ray collecting device 2 and/or an artificial light ray source 3. The bioreactor is constructed in such a manner that the light rays transmitted through the optical conductor 4 are emitted from the light radiator in the reactor 1, and preferably the light rays are emitted uniformly throughout the reactor 1. Furthermore, the internal space of the reactor is kept in an optimum condition for propagating micro-organisms by means of a density analyzer 8, an oxygen analyzer 9, and further, a culture fluid testing device 10 for detecting other conditions of the culture fluid.

Furthermore, in order to effectively cultivate micro-organisms, an adequate amount of carbon dioxide $CO_2$ needs to be supplied to the micro-organisms in the tank in addition to the aforementioned conditions. However, it is very difficult to effectively dissolve carbon dioxide $CO_2$ in a culture fluid. As mentioned before, the micro-organisms are destroyed by such bubbling.

Furthermore, in space, it is impossible to bubble the liquid because mist is generated instead, and the micro-organisms are also destroyed.

The present invention was made for the purpose of effectively dissolving carbon dioxide in a culture fluid, and a gas-exchanger 5 is installed for that purpose.

Figure 2:
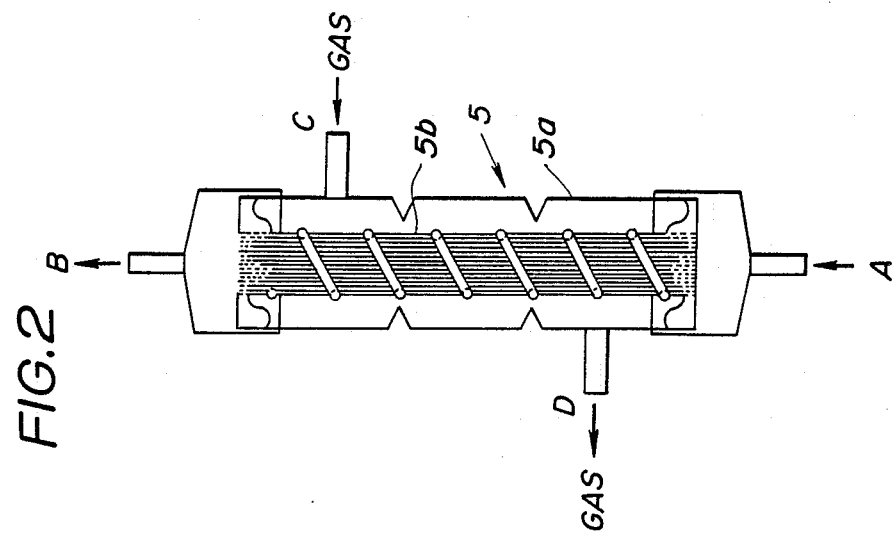
FIG. 2 is a detailed cross-sectional view of the $CO_2$ gas-exchanger shown in FIG. 1.

FIG. 2 is a detailed cross-sectional view of the gas-exchanger 5 shown in FIG. 1. The gas-exchanger 5 consists of a hermetically sealed tank 5a and a large number of hollow pipes 5b made of silicone rubber which are arranged by placing them inside of the tank 5a. Micro-organisms suspension or culture medium in the bioreactor 1 is supplied to the hollow pipes 5b as shown in FIG. 1, and the same is returned to the bioreactor 1 through the pipe 12.

Moreover, in the case of employing a pipe made of silicone rubber as the hollow pipes 5b, it is possible to autoclave it or to clean it by the use of a chemical which is preferable for such pipes 5b. And further, carbon dioxide $CO_2$ is supplied to the hermetically sealed tank 5a from a $CO_2$ gas-supplying source 11 as shown in FIG. 1, in which the gas pressure of the $CO_2$ gas is higher than the pressure in the hollow pipes 5b. And further, the hollow pipes 5b have a large number of microscopic holes such that the $CO_2$ gas infiltrates into the pipes 5b through the microscopic holes and is dissolved in the culture medium flowing inside the pipes 5b.

Figure 3:
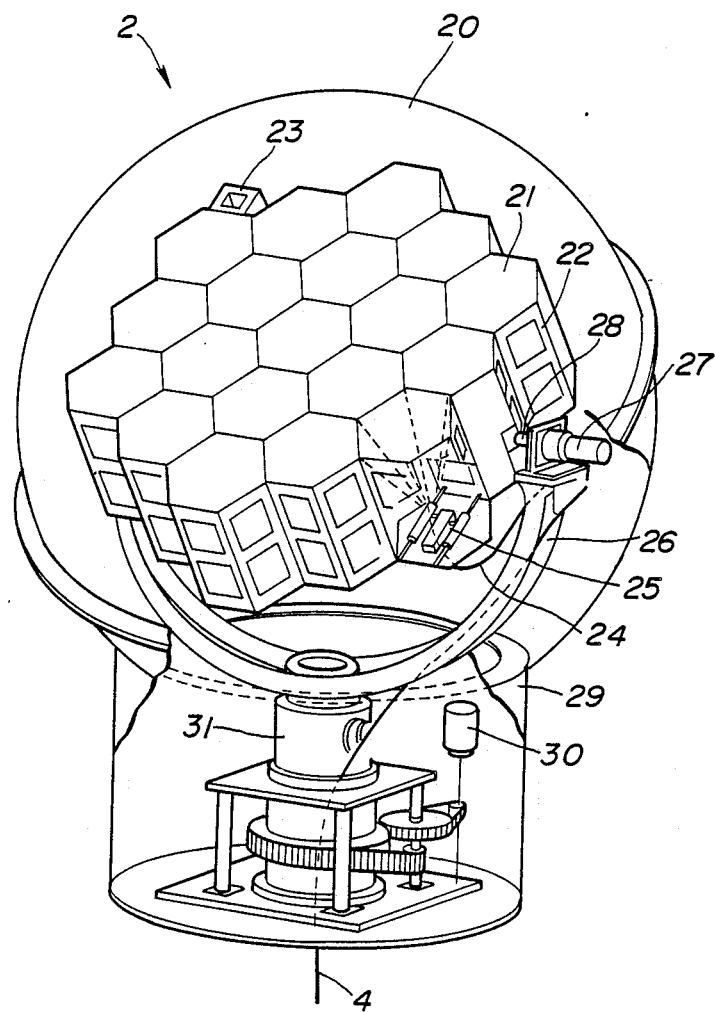
FIG. 3 is a detailed perspective view for explaining an embodiment of a solar ray collecting device.

FIG. 3 is a detailed perspective view for explaining an embodiment of a solar ray collecting device 2 shown in FIG. 1. In FIG. 3, 20 is a transparent protective capsule, 21 a Fresnel lens, 22 a lense holder, 23 a sensor for sensing the direction of the solar rays, 24 an optical fiber having a light-receiving end disposed at the focal position of the Fresnel lense 21, 25 a fiber holder, 26 an arm, 7 a pulse motor, 28 a horizontal rotating shaft driven by the pulse motor 27, 29 a foundation for carrying the protective capsule 20, 30 a pulse motor, and 31 a vertical rotating shaft driven by the pulse motor 30.

As already proposed by the present applicant, the above-mentioned solar ray collecting device senses the direction of the solar rays from the sun by means of the solar-ray direction sensor 23. The detection signal generated by the sensor 23 controls the pulse motors 27 and 30 for driving the horizontal rotating shaft 28 and the vertical rotating shaft 31 respectively, so as to turn the sensor 23 towards the sun. Thereby, the solar rays focused by the respective lenses 21 are guided into the respective optical fibers 24 having a light-receiving end disposed at the focal position of the respective lenses.

The optical fibers 24, respectively disposed as set forth above for each lense, are collectively tied up in a bundle and led out from the solar ray collecting device 2, as the optical conductor cable 4 shown in FIG. 1, and is connected with the bioreactor 1.

Figure 4:
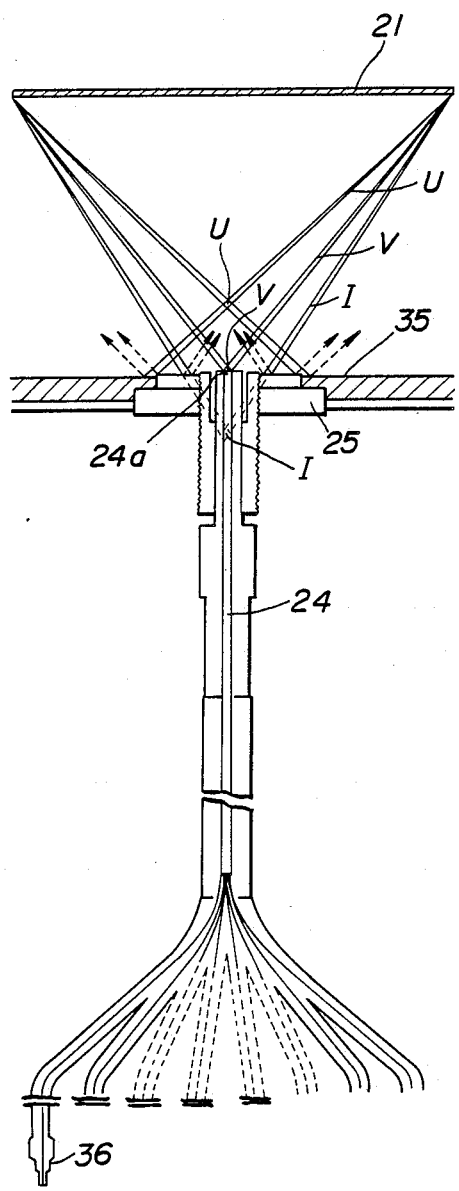
FIG. 4 is a cross-sectional view for explaining the operational principle for guiding the light rays consisting of visible light ray components into the optical conductor.

FIG. 4 is a cross-sectional view for explaining the relationship of the Fresnel lense 21 and the optical fiber 24, both of which are shown in FIG. 3. In FIG. 4, U represents the focal point of the ultraviolet rays contained in the solar rays, V the focus of the visible light rays, and I the focus of the infrared rays. As shown in FIG. 4, when the light-receiving end 24a of the optical fiber 24 is located at the focal position of the visible light rays, only the visible light rays containing neither ultraviolet nor infrared rays are guided into the optical fiber 24.

In FIG. 4, 35 is a reflecting plate. At the time of locating the light-receiving end 24a of the optical fiber 24 at the focal position of the Fresnel lense 21, as regards the visible light ray components, the reflecting plate 35 is placed for the purpose of preventing light rays of a high-energy density from being focused by the Fresnel lense 21 and from being radiated onto the working personnel.

Figure 5B:
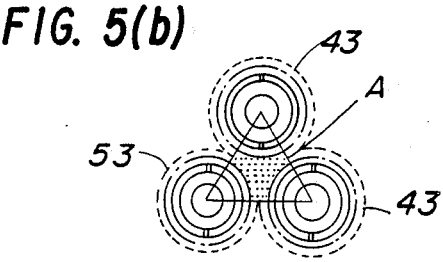
Figure 5A:
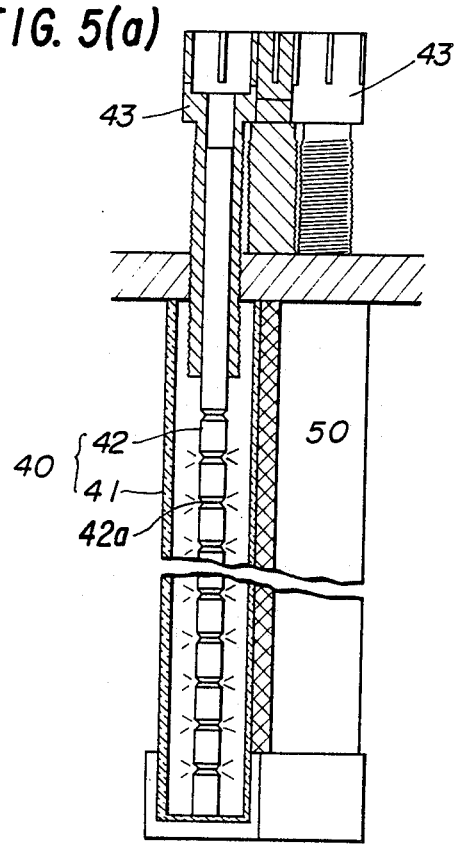

FIGS. 5a and 5b are cross-sectional construction views for explaining an embodiment of a light radiator used for emitting light rays transmitted through the optical fiber in the bioreactor 1 shown in FIG. 1. FIG. 5a is a side, cross-sectional view of the light radiator, and FIG. 5b is a plane view thereof. In FIG. 5a, 41 is a transparent tube and 42 an optical conductor rod placed in the tube 41. As previously proposed by the present applicant, the light radiator 40 is constructed of a transparent tube 41 and an optical conductor rod 42. A large number of light radiators 40, constructed as mentioned before, are closely arranged parallel to each other in the bioreactor 1, as shown in FIG. 5b.

In FIG. 5a, 43 is a fiber connector. The fiber connector 36, shown in FIG. 4, is connected with the connector 43. When those connectors 36 and 43 are connected to each other, the visible light rays guided into the optical conductor 24, as mentioned before, are transmitted to the optical conductor rod 42 through this connection. The transmitted visible light rays are emitted outside of the optical conductor rod 42 from the light-emitting portion 42a of the optical conductor 42.

Suspended micro-organisms 50 fill the space between the respective light radiators arranged as mentioned above and as indicated by the dotted area A shown in FIG. 5b. The light rays emitted from the light radiator 40 as mentioned before, are supplied to micro-organisms suspension 50, and photo-synthesis of the micro-organisms thereby takes place.

On the other hand, in the bioreactor previously proposed by the present applicant, bubbling is performed by supplying under pressure, air containing carbon dioxide $CO_2$ from the lower side into the aforementioned suspended micro-organisms 50. However, the micro-organisms are destroyed by bubbling and carbon dioxide $CO_2$ cannot be effectively dissolved in the ground cultures.

Furthermore, in the case of employing the abovementioned bioreactor in gravity-less places, such as in space or the like, bubbling cannot be performed and the carbon dioxide $CO_2$ turns into mist. On such occasion, there still exists the problem that the micro-organisms are destroyed. To the contrary, according to the present invention, carbon dioxide $CO_2$ can be effectively dissolved in the micro-organism suspension and will not bubble. As a result, cultivation of the micro-organisms can be effectively carried out, and even in space, the micro-organisms, can be effectively cultivated.

As is apparent from the foregoing description, according to the present invention, carbon dioxide $CO_2$ is dissolved in micro-organisms suspension or culture medium by the action of the pressure difference between the pressure of micro-organisms suspension or culture medium flowing in the porous silicone pipes and the pressure of the carbon dioxide $CO_2$ supplied to the outside of the porous silicone pipes. Namely, the carbon dioxide $CO_2$ is dissolved therein without bubbling. Therefore, the micro-organisms are not destroyed, and even in universal space carbon dioxide $CO_2$ can be effectively dissolved in the micro-organisms suspension or culture medium.

I claim:

1. Photosynthesis apparatus comprising a bioreactor tank means containing a culture fluid, light radiator means disposed in said tank means, said light radiator means comprising a plurality of transparent cylinder bodies disposed parallel to one another, said light radiator means further comprising optical conductors disposed in each of said cylindrical bodies, solar ray collecting means for guiding light rays into said optical conductors, said tank means being elongated and having a longitudinal axis, said longitudinal axis being vertically disposed, said tank means having an upper end and a lower end, said tank means having an upper end portion juxtaposed to said upper end, said tank means having a first outlet for said culture fluid, said first outlet being located at said upper end portion, gas-exchanger means for supplying carbon dioxide, said gas-exchanger means having a first inlet for said culture fluid, a first conduit between said first outlet and said first inlet, a pump in said first conduit for pumping culture fluid from said tank means to said gas-exchanger means via said first conduit, said tank means having a second inlet for said culture fluid, said second inlet being located at said lower end of said tank means, said gas-exchanger means having a second outlet for said culture fluid, a second conduit between said second outlet and said second inlet for conducting culture fluid from said gas-exchanger means to said tank means, said gas-exchanger means comprising a hermetically sealed container means and a plurality of porous pipes having microscopic holes disposed in said container means, said culture fluid passing through the interior of said porous pipes, and carbon dioxide supply means for supplying carbon dioxide to said container means and to the exterior of said porous pipes at a pressure higher than the pressure of said culture fluid in the interior of said porous pipes such that the carbon dioxide infiltrates through the microscopic holes in said porous pipes to be dissolved in the culture fluid in said porous pipes, said gas-exchanger means, said first and second conduits, and said pump means defining a closed recycling means for recycling said culture fluid such that a part of said culture fluid is recycled through said closed recycling means to be replenished with said carbon dioxide as said culture fluid flows through said closed recycling means.

2. Bioreactor apparatus according to claim 1 wherein said light source means guides the visible light ray components of solar rays to said optical conductors.

3. Bioreactor apparatus according to claim 1 wherein said light source means guides the visible light ray components of artificial light rays to said optical conductors.

4. Bioreactor apparatus according to claim 1 wherein said porous pipes in said gas-exchanger means comprise silicone pipes.

5. Bioreactor apparatus according to claim 1 wherein said porous pipes in said gas-exchanger means are made of silicone rubber.

* * * * *